US006074986A

United States Patent [19]

Mulqueen et al.

[11] Patent Number: 6,074,986

[45] Date of Patent: *Jun. 13, 2000

[54] STORAGE AND DILUTION OF STABLE AQUEOUS DISPERSIONS

[76] Inventors: Patrick Joseph Mulqueen, 8 Sewell Close, Abington Oxon OX14 3YJ; Steven Duff Lubetkin, 24 Haywards Close, Wantage Oxon, OX12AT; Graham Banks, 12 Craven Common, Uffington Farington, Oxon SN7 7RN; Andrew Mark Fowles, 37 Midwinter Avenue, Cherry Orchard, Milton Heights Oxon, OX14 3XB, all of United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/615,326

[22] PCT Filed: Sep. 14, 1994

[86] PCT No.: PCT/US94/10416

§ 371 Date: Aug. 2, 1996

§ 102(e) Date: Aug. 2, 1996

[87] PCT Pub. No.: WO95/07614

PCT Pub. Date: Mar. 23, 1995

[30] Foreign Application Priority Data

Sep. 15, 1993 [GB] United Kingdom .................. 9319129

[51] Int. Cl.$^7$ .............................. A01N 25/04; B01F 3/08

[52] U.S. Cl. ............................. 504/116; 424/405; 516/53

[58] Field of Search ............................ 504/116; 252/311, 252/314, 352, 353; 514/938, 963, 970; 516/53; 424/405

[56] References Cited

U.S. PATENT DOCUMENTS 5,371,105 12/1994 Damo ..................................... 514/469

FOREIGN PATENT DOCUMENTS

| | | |
|---|---|---|
| 0357559 | 3/1990 | European Pat. Off. . |
| 0379851 | 8/1990 | European Pat. Off. . |
| 0589838 | 3/1994 | European Pat. Off. . |
| WO89/03175 | 4/1989 | WIPO . |
| WO92/09197 | 6/1992 | WIPO . |
| WO93/15605 | 8/1993 | WIPO . |

OTHER PUBLICATIONS

S. S. Davis and A. Smith, "The Influence of the Disperse Phase on the Stability of Oil–in–Water Emulsions", *Theory and Practice of Emulsion Technology,* Academic Press, London, 1974.

S. Wang and F. J. Schork, *Journal of Applied Polymer Science,* 54, 2157–2164 (1994).

*Primary Examiner*—S. Mark Clardy
*Attorney, Agent, or Firm*—Craig E. Mixan

[57] ABSTRACT

A formulation e.g., a pesticidal formulation in the form of a dispersion comprising a continuous aqueous phase, and a discontinuous phase comprising a non-aaueous material capable of transport through the aqueous phase to cause Ostwald ripening of the dispersion, wherein there is contained within the discontinuous phase a pesticidal material, which may or may not be the said non-aqueous material, wherein the discontinuous phase comprises a stabiliser in an amount sufficient to depress migration of the non-aqueous material through the aqueous phase, and thereby diminish or prevent Ostwald ripening of the dispersion, characterised in that the stabiliser has a molecular weight of not more than 10,000, and is soluble in the discontinuous phase, but insoluble in and not transportable through the aqueous phase. The production of the formulation can be carried out in a metered in-line mixing plant, since the thermodynamics of the mixing process is such that the particle size tends to a predictable value.

19 Claims, No Drawings

STORAGE AND DILUTION OF STABLE AQUEOUS DISPERSIONS

This application has been filed under 35 USC 371 on the national stage of international application PCT/US 94/10416, filed Sep. 14, 1994.

This invention relates generally to the preparation of queous dispersions, which term is used herein to include both dispersions of solid particles, and in particular, aqueous emulsions, which are stable on storage and dilution, and in particular to the preparation of emulsions containing pesticides, for example herbicides, insecticides, or fungicides which are stable on storage and dilution.

The continuing emphasis on environmental pollution caused by the use of organic solvents makes it increasingly desirable to prepare various formulations as emulsion preparations, rather than as solutions in organic solvents. There are very many examples of this, for example in the preparation of adhesives and the like. A particularly important area is in the field of pesticidal compositions, for example herbicidal, insecticidal, or fungicidal compositions, in which large quantities of solvent typically need to be employed in order to present the active materials at the desired rate of application, to the intended locus.

Although many pesticidal materials are readily emulsifiable, problems arise in the preparation of concentrates of dispersed pesticides (particularly emulsions) which are both storage stable, and stable on dilution prior to application.

Emulsion formulations can be caused to become unstable for a variety of reasons. The most important of these may be summarized as follows:

1. External force fields such as gravitational or centrifugal fields;
2. Flocculation resulting from attractive forces between the droplets;
3. Mechanical aggregation of droplets to form larger droplets, and ultimately to immiscible bulk liquids;
4. So called "Ostwald ripening" in which a component of the disperse phase migrates through the continuous phase between particles of the dispersed phase, thus allowing a change in overall particle size distribution.
5. Coalescence resulting from a combination of the above.

This invention is concerned with diminishing or preventing Ostwald ripening as a cause of emulsion instability.

Ostwald ripening can occur whenever a component of the disperse phase is capable of being transported through the continuous phase from one particle to another. The usual mechanism for such transport is by dissolution of the transportable material in the continuous phase, which can occur even if the solubility of the material is low. Other transport mechanisms are however possible. For example, even materials having a very low water solubility indeed, which might not be expected to display Ostwald ripening, can do so, when certain surfactants are used in the preparation and stabilization of the emulsion. This is believed to be due to transport of the water insoluble materials through the aqueous phase by dissolution in surfactant micelles.

The direction of migration of the non-aqueous phase tends to be from smaller particles to larger particles, because of the respective chemical potential of the non-aqueous materials in the emulsion particles. Thus, the overall effect of the migration of materials between the emulsion particles is to tend to cause the particle size distribution to shift towards larger particle sizes, which is very disadvantageous in many cases.

Various attempts have been made to control Ostwald ripening of emulsions. For example, U.S. Pat. No. 4,348,385 (Mobay Chemical) is concerned with the control of Ostwald ripening of a dispersion of a solid pesticide material in an organic solvent. The proposed solution to the problem of Ostwald ripening of the solid pesticide dispersion is the addition of a solid ionic dispersant.

W092/09197 (KVK Agro) is concerned with the preparation of a herbicidal composition containing a solid herbicide dispersed in a liquid. The product is stabilised on dilution by the addition of a water-soluble polymer to the herbicide concentrate. The concentrate is not an oil-in-water emulsion, and the water-soluble polymer stabiliser acts as a dilution aid, on addition of the concentrate to water.

W089/03175 (Dow Chemical) is concerned with the production of water diluable pesticide compositions, which are stabilised by the addition of a polymer latex. The polymer latex comprises solid particles insoluble in the solvents employed.

W093/15605 (Schering Agrochemicals) discloses pesticidal emulsions, to which are added a crystallisation inhibitor which is an aromatic compound or an aliphatic carboxylic acid.

EP-A-0357559 (Ciba Geigy) discloses the addition of crystallisation inhibitors (mainly phenols and alcohols) to emulsions of pesticides such as Furathicocarb which have a tendency to crystallise on storage when formulated without solvents. The mode of action is unclear but would appear to be a plasticising effect of the phenol on the pesticide.

EP-A-0397851 (Monsanto) discloses the use of a long chain fatty oil, such as a long chain fatty acid as an additive to pesticidal compositions.

EP-A-0589838 (Ciba Geigy) is concerned with the production of pesticidal compositions comprising an organic phase containing a substantially hydrophobic pesticide dissolved in a hydrophobic solvent, and an aqueous phase containing surfactants and/or dispersants. The composition contains a stabiliser, which is a polymer or polymer mixture which is more soluble in the organic phase than in the aqueous phase. The polymers employed are said to be "more soluble in the organic phase than in the aqueous phase", and although there is some reference to polymers which are "substantially insoluble in water" many of the preferred materials have substantial water solubility, and the general levels of water insolubility contemplated are not so low as only a few parts per million. The polymers are also said to "dissolve in the pesticide or solution of the pesticide in a hydrophobic solvent, thereby increasing its viscosity". They are specifically required to have a molecular weight of from 10,000 to 1,000,000 daltons. The stabilised emulsions are prepared by dissolving the polymeric stabiliser in the pesticidal substance, and subsequently converting the mixture to a fine-particle emulsion using a high shear mixer.

In accordance with a first aspect of the invention, we have now surprisingly determined that materials which would not be expected from EP-A-0589838 to be effective as emulsion stabilisers are very effective indeed in the stabilisation of aqueous emulsions against Ostwald ripening, and can diminish or entirely prevent Cstwald ripening occurring. Specifically, polymeric materials having a molecular weight of not more than 10,000, and which are soluble in the discontinuous phase of the emulsion, but insoluble in and not transportable through the aqueous phase are effective in providing such stabilisation.

Accordingly, in a first aspect of the invention, there is provided a two phase dispersion, for example an aqueous emulsion, comprising a continuous aqueous phase and a discontinuous phase comprising a non-aqueous material capable of transport through the aqueous phase to cause Ostwald ripening of the dispersion, wherein the discontinuous phase comprises a stabiliser in an amount sufficient to depress migration of the non-aqueous material through the aqueous phase, and thereby diminish or prevent Ostwald ripening of the dispersion, wherein the stabiliser has a molecular weight of not more than 10,000, and is soluble in the discontinuous phase, but insoluble in and not transportable through the aqueous phase.

The invention also provides a method of preparing such a two phase dispersion comprising a continuous aqueous phase and a discontinuous non-aqueous phase comprising a substance capable of transport through the aqueous phase to cause Ostwald ripening of the dispersion, which method comprises dispersing a non-aqueous phase comprising the said substance and a dissolved stabiliser in water in the presence of a surfactant wherein the stabiliser has a molecular weight of not more than 10,000, and is soluble in the discontinuous phase, but insoluble in and not transportable through the aqueous phase.

In accordance with a second aspect of the invention, we have discovered that whether use is made of stabilisers having a molecular weight of less than 10,000, or the higher molecular weight szabiliser materials employed in EP-A-0589838 it is not necessary to dissolve the polymeric stabiliser in the organic phase, and subsequently convert the mixture to a fine-particle emulsion using a high shear mixer as required by EP-A-0589838, in order to prepare emulsions which are stable against Ostwald ripening. To the contrary, we have found to our surprise that if as a first step, a "template dispersion" of the stabiliser in water is formed, in the presence of a suitable surfactant, in which the dispersed phase contains the stabiliser preferably dissolved in a non-aqueous solvent, the other non-aqueous components (in particular, when the composition is a pesticidal composition, the pesticide-containing component) need not be added under high shear, or indeed under shear at all, but can even be added to the template emulsion in bulk. Whatever the method of addition, the said non-aqueous components added after formation of the template dispersion become incorporated into the particles of the template dispersion, increasing the particle size of the dispersion by a consistent and predictable amount.

Accordingly, in a second aspect of the invention, there is provided a method of preparing a two phase dispersion comprising a continuous aqueous phase and a discontinuous non-aqueous phase comprising a substance capable of transport through the aqueous phase to cause Ostwald ripening of the dispersion, which method comprises dispersing in water in the presence of a surfactant a non-aqueous phase comprising the dissolved stabiliser, and adding the said substance to the resulting dispersion such that the said substance and the stabiliser are incorporated in the non-aqueous phase of the dispersion.

The discontinuous phase of the resulting dispersion generally comprises the material which it is desired to disperse, for example the pesticide when the invention is employed in the formulation of pesticide concentrates.

In a further preferred and specific embodiment, the invention provides a method for the preparation of a pesticidal formulation, which method comprises dispersing in water in the presence of a surfactant a non-aqueous phase comprising the stabiliser and optionally a non-aqueous solvent, and adding to the resulting dispersion a pesticide and optionally a non-aqueous solvent, such that the pesticide and added non-aqueous solvent (if any) are incorporated in the non-aqueous phase of the dispersion.

In a further embodiment, polymerizable monomers may be employed (optionally containing pesticide) such that by incorporating the monomers into the non-aqueous phase and subsequently polymerising the monomer, particles can be produced with very controllable particle size distributions. The particle size can be predicted accurately by calculation of the anticipated volume increase on addition of the polymerizable material and a knowledge of the template size and quantity. Such products have utility as a controlled release vehicle, the pesticide (or other active material) releasing from a polymeric matrix. By repeat processes (optionally with different monomers) core-shell products may be easily constructed.

The stabilizer which is employed in accordance with the present invention is a material which is soluble, preferably soluble in all proportions, in the discontinuous (non-aqueous) phase, but which is insoluble in, and not transportable through, the aqueous phase.

The terms "discontinuous phase" or "disperse phase" as used herein refer to the droplet or particulate phase, and the continuous (aqueous) phase refers to the suspending medium.

As indicated above, by "not transportable" through the aqueous phase is meant that not only does the stabilizer not dissolve in the aqueous phase, also its solubility in any micelles present, as a consequence of surfactants employed in the emulsification, is such that the transport of the stabilizer through the aqueous phase in micelles also does not occur to a significant degree. The water solubility of the stabilizer is preferably not more than 100 ppm by weight, more preferably not more than 10 ppm, most preferably not more than 1 ppm.

The presence of the stabilizer in the discontinuous phase has the effect of modifying the chemical potential of the various components of the discontinuous (non-aqueous) phase, such that resultant net transport of the non-aqueous material through the aqueous phase is diminished or prevented.

A pesticidal formulation in accordance with the invention generally comprises a continuous aqueous phase, and a discontinuous phase comprising a non-aqueous material capable of transport through the aqueous phase to cause Ostwald ripening of the dispersion. This material will often be a non-aqueous solvent in which the active (for example pesticidal material) is dissolved, but may be the pesticidal material itself.

The discontinuous phase comprises a stabiliser as described, i.e., one which is soluble in the discontinuous phase, but insoluble in and not transportable through the aqueous phase. The amount of stabiliser present is sufficient to depress migration of the non-aqueous solvent through the aqueous phase, and thereby diminish or prevent Ostwald ripening of the dispersion.

A further aspect provides the use of a stabiliser as defined herein in the preparation of a two phase dispersion comprising a continuous aqueous phase and a discontinuous non-aqueous phase including a substance capable of transport through the aqueous phase to cause Ostwald ripening of the dispersion.

The stabilizer may be any material which is soluble in the non-aqueous phase, but insoluble in (and not transportable through) the aqueous phase.

Although it is not intended to be bound by any theory of operation, it is believed that the stabilization of the dispersion is caused by the effect which the stabilizer has on the chemical potential of the composition. In a normal emulsion (without the stabilizer present) any materials present in the non-aqueous phase which are capable of migration through the aqueous phase, whether by solution in it, or by micelle transport, tend to migrate from the smaller to larger size particles because migration in this direction results in a decrease in the overall free energy of the system. With the stabilizer present however, this tendency is countered, because migration of materials from droplets or particles in the non-aqueous phase tends to raise the concentration of the stabilizer in the respective smaller particles, and hence to change the chemical potential. The overall effect is that the dispersion tends to a particle size distribution which is stable, so far as we have been able to ascertain, for an indefinite period.

This characteristic of the dispersions in accordance with the invention opens up a number of interesting possibilities, particularly in the field of the commercial production of emulsion preparations. In general when commercial emulsions are prepared, the particle size must be carefully controlled during the production process, in order that the commercial product should be consistent. The need for accurate particle size makes it difficult or impossible to employ metered in-line mixing for the production of commercial emulsions, since any variation of particle size is likely to have entered the packaging line, before the necessary corrective action can be taken. For this reason, production of commercial emulsions is carried out almost universally on a batch basis.

In accordance with one aspect of the method of the invention, an emulsion may be formed of a desired material by forming a template emulsion comprising in its non-aqueous phase a stabilizer of the kind described above and optionally one or more other components, such as non-aqueous solvents, and combining the template emulsion with the material of which it is desired to form an emulsion. The said material may be added without dilution, in the form of a solution in a non-aqueous solvent, or as an emulsion with the material in the non-aaueous phase. The result of the combination is that the non-aqueous phase containing the material migrates to the template emulsion, to form an emulsion comprising the said material and the stabilizer in this non-aqueous phase. This process can be carried out in a metered in-line mixing plant, since the thermodynamics of the mixing process is such that the particle size tends to a predictable value.

Examples of suitable stabilising materials for use in the second aspect of the invention are polymers or oligomers having a molecular weight from 250 to $10^6$, preferably 400 to $10^5$, more preferably 400 to $10^4$. The stabilising materials used in the first aspect of the invention are polymers or oligomers having a molecular weight from 250 to $10^4$. The chemical composition of the material will depend upon the need to be soluble in the dispersed phase. Suitable materials may be homopolymers or co-polymers, for example those described in "Polymer Handbook" 3rd Edition edited by J. Brandrup and E. H. Immergut. Examples of suitable homopolymers include polyolefins such as polyallene, polybutadiene, polyisoprene, and poly(substituted butadienes) such as poly(2-t-butyl-1,3-butadiene), poly(2-chlorobutadiene), poly(2-chloromethyl butadiene), polyphenylacetylene, polyethylene, chlorinated polyethylene, polypropylene, polybutene, polyisobutene, polybutylene oxides, or copolymers of polybutylene oxides with propylene oxide or ethylene oxide, polycyclopentylethylene, polycyclolhexyiethylene, polyacrylates including polyalkylacrylates and polyarylacrylates, polymethacrylates including polyalkylmethacrylates and polyarylmethacrylates, polydisubstituted esters such as poly(di-n-butylitaconate), and poly(amylfumarate), polyvinylethers such as poly(butoxyethylene) and poly(benzyloxyethylene), poly(methyl isopropenyl ketone), polyvinyl chloride, polyvinyl acetate, polyvinyl carboxylate esters such as polyvinyl propionate, polyvinyl butyrate, polyvinyl caprylate, polyvinyl laurate, polyvinyl stearate, polyvinyl benzoate, polystyrene, poly-t-butyl styrene, poly (substituted styrene), poly(biphenyl ethylene), poly(1,3-cyclohexadiene), polycyclopentadiene, polyoxypropylene, polyoxytetramethylene, polycarbonates such as poly(oxycarbonyloxyhexamethylene), polysiloxanes, in particular, polydimethyl cyclosiloxanes and organo-soluble substituted polydimethyl siloxanes such as alkyl, alkoxy, or ester substituted polydimethylsiloxanes, liquid polysulfides, natural rubber and hvdrochlorinated rubber, ethvi-, butyl- and benzyl-celluloses, cellulose esters such as cellulose tributyrate, cellulose tricaprylate and cellulose tristearate and natural resins such as colophony, copal and shellac.

Examples of suitable co-polymers are co-polymers of styrene, alkyl styrenes, isoprene, butenes, butadiene, acrylonitrile, alkyl acrylates, alkyl methacrylates, vinyl chloride, vinylidene chloride, vinyl esters of lower carboxylic acids and alpha, beta-ethylenically unsaturated carboxylic acids and esters thereof, including co-polymers containing three or more different monomer species therein.

Other suitable polymers are those polymers which can also function as surfactants, but yet are insoluble in the continuous phase. These include for example:

nonionic polyalkylene glycol alkyd compounds prepared by reaction of polyalkylene glycols and/or polyols with (poly)carboxylic acids or anhydrides, A-B-A block-type surfactants such as those produced from the esterification of poly(12-hydroxystearic acid with polyalkylene glycols.

High molecular weight esters of natural vegetable oils such as the alkyl esters of oleic acid and polyesters of polyfunctional alcohols may also be employed.

Preferred stabilisers are polystyrenes, polybutenes, for example polyisobutenes, polybutadienes, polypropylene glycol, methyl oleate, polyalkyl(meth)acrylate e.g. polyisobutylacrylate or polyoctadecylmethacrylate, polyvinylesters e.g. polyvinylstearate, polystyrene/ethyl hexylacrylate copolymer, and polyvinylchloride, polydimethyl cyclosiloxanes, organic soluble substituted polydimethyl siloxanes such as alkyl, alkoxy or ester substituted polydimethylsiloxanes, and plybutylene oxides or copolymers of polybutylene oxides with propylene and/or ethylene oxide.

The stabilizer is generally used as a pre-prepared polymer or oligomer. In an alternative embodiment however, the stabilizer may be prepared in situ by polymerization of one or more appropriate monomers with the non-aqueous phase, during preparation of the dispersion.

The stabilizer may be employed in an amount of from 0.1 to 90, preferably from 0.5 to 50 percent by weight of the disperse phase. Mixtures of stabilIzers may be employed.

Surfactants which can be advantageously employed herein can be readily determined by those skilled in the art and include various nonionic, anionic, cationic, or amphoteric surfactants, or a blend of two or more surfactants may be employed. Preferred surfactants are those which significantly reduce the interfacial tension between the aqueous phase and dispersed phase, and thereby reduce the tendency for droplet coalescence. We have found that the use of the stabilizers described above with such surfactants can produce even greater reduction in the tendency for droplet coalescence.

Examples of nonionic surfactants useful in preparing the oil-in-water emulsion include the polyalkylene glycol ethers and condensation products of alkyl phenols, aliphatic alcohols, aliphatic amines or fatty acids with ethylene oxide, propylene oxide or mixtures of ethylene and propylene oxides such as the ethoxylated alkyl phenols or ethoxylated aryl or polyaryl phenols and carboxylic esters solubilized with a polyol or polyvinyl alcohol/polyvinyl acetate copolymers (PVA). Cationic emulsifiers include quaternary ammonium compounds and fatty amines. Anionic emulsifiers include the oil-soiuble (eg. calcium, ammonium) salts of alkyl aryl sulphonic acids, oil soluble salts of suiphated polyglycol ethers, salts of the ethers of suiphosuccinic acid, or half esters thereof with nonionic surfactants and appropriate salts of phosphated polyglycol ethers. Preferred emulsifiers are those which form and stabilise oil-in-water emulsions such as ethoxylated alcohols, alkoxylated alkyl phenols or polyalkylene oxide copolymers and PVAs. The surfactant is generally employed in an amount of from 0.1 to 15 percent, more preferably from 2 to 10 percent, and most preferably about 5 percent by weight of the total composition.

The discontinuous phase may consist simply of the material which it is desired to emulsify (for example the pesticide) together with the stabilizer.

In a preferred embodiment however, the discontinuous phase may also comprise a water-immiscible solvent, and indeed in many cases, the water-immiscible solvent will be the material prone to cause Ostwald ripening. Examples of typical solvents are aromatic solvents, particularly alkyl substituted benzenes such as xylene or propyl benzene fractions, and mixed naphthalene and alkyl naphthalene fractions; mineral oils; kerosene, dialkyl amides of fatty acids, particularly the dimethyl amides of fatty acids such as the dimethyl amide of caprylic acid; chlorinated aliphatic and aromatic hydrocarbons such as 1,1,1-trichloroethane and chlorobenzene, esters of glycol derivatives, such as the acetate of the n-butyl, ethyl, or methyl ether of diethyleneglycol, the acetate of the methyl ether of dipropyleneglycol, ketones such as isophorone and trimethylcycichexanone (dihydroisophorone) and the acetate products such as hexyl, or heptylacetate. The preferred organic liquids are xylene, propyl benzene fractions, alkyl acetates, and alkyl naphthalene fractions.

It may also be desirable in certain applications to dissolve the stabilizer in a relatively low boiling point solvent, in order to ease the processing, and subsequently to evaporate the low boiling point solvent at a later stage of the processing procedure.

The preparation methods of the present invention are preferably carried out at a temperature of from ambient to 70° C., more preferably ambient to 50° C. The precise temperature chosen will depend upon the melting points of the material which it is desired to incorporate.

Pesticidal substances suitable for use in the composition in accordance with the invention include the following insecticides:

| | |
|---|---|
| amitraz | fenobucarb |
| azinphos-ethyl | gamma-HCH |
| azinphos-methyl | methidathion |
| benzoximate | deltamethrin |
| bifenthrin | dicofol |
| binapacryl | dioxabenzafos |
| bioresmethrin | dioxacarb |

-continued

| | |
|---|---|
| chlorpyrifos | endosulfan |
| chlorpyrifos-methyl | EPNethiofencarb |
| cyanophos | dinobuton |
| cyfluthrin | tetradifon |
| cypermethrin | tralomethrin |
| bromophos | N-2,3-dihydro-3-methyl-1,3- |
| bromopropylate | thiazol-2-ylidene-2,4- |
| butacarboxim | xylidene |
| butoxycarboxin | parathion methyl |
| chlordimeform | phosalone |
| chlorobenzilate | phosfolan |
| chloropropylate | phosmet |
| chlorophoxim | promecarb |
| fenamiphos | quinalphos |
| resmethrin | |
| temephos | pirimiphos-ethyl |
| tetramethrin | pirimiphos-methyl |
| xylylcarb | profenofos |
| acrinathrin | propaphos |
| allethrin | propargite |
| benfuracarb | propetamphos |
| bioallethrin | pyrachlofos |
| bioallethrin S | tefluthrin |
| bioresmethrin | terbufos |
| buprofezin | tetrachlorinphos |
| chlorfenvinphos | tralomethrin |
| chlorflurazuron | triazophos |
| chlormephos | pyrachlofos |
| cycloprothrin | tefluthrin |
| betacyfluthrin | terbufos |
| cyhalothrin | tetrachlorinphos |
| cambda-cyhalothrin | tralomethrin |
| alpha-cypermethrin | triazophos |
| beta-cypermethrin | |
| cyphenothrin | |
| demeton-S-methyl | |
| dichlorvos | |
| disulfoton | |
| edifenphos | |
| empenthrin | |
| esfenvalerate | |
| ethoprophos | |
| etofenprox | |
| etrimphos | |
| fenazaquin | |
| fenitrothion | |
| fenthiocarb | |
| fenpropathrin | |
| fenthion | |
| fenvalerate | |
| flucythrinate | |
| flufenoxuron | |
| tau-fluvalinate | |
| formothion | |
| hexaflumuron | |
| hydroprene | |
| isofenphos | |
| isoprocarb | |
| isoxathion | |
| malathion | |
| mephospholan | |
| methoprene | |
| methoxychlor | |
| mevinphos | |
| permethrin | |
| phenothrin | |
| phenthoate | |

the following fungicides:-

| | |
|---|---|
| benalaxyl | biteranol |
| bupirimate | cyproconazole |
| carboxin | tetraconazole |
| dodemorph | difenoconazole |
| dodine | dimethomoph |
| fenarimol | diniconazole |
| ditalimfos | ethoxyquin |
| myclobutanil | etridiazole |
| nuarimol | fenpropidin |
| oxycarboxin | fluchloralin |

-continued

| | |
|---|---|
| penconazole | flusilazole |
| prochloraz | imibenconazole |
| tolclofos-methyl | myclobutanil |
| triadimefon | propiconazole |
| triadimenol | pyrifenox |
| azaconazole | tebuconazole |
| epoxyconazole | tridemorph |
| fenpropimorph | triflumizole |
| the following herbicides:- | |
| 2,4-D esters | diclofop-methyldiethatyl |
| 2,4-DB esters | dimethachlor |
| acetochlor | dinitramine |
| aclonifen | ethalfluralin |
| alachlor | ethofumesate |
| anilophos | fenobucarb |
| benfluralin | fenoxaprop ethyl |
| benfuresate | fluazifop |
| bensulide | fluazifop-P |
| benzoylprop-ethyl | fluchloralin |
| bifenox | flufenoxim |
| bromoxynil esters | flumetralin |
| bromoxynil | flumetralin |
| butachlor | fluorodifen |
| butamifos | fluoroglycofen ethyl |
| butralin | fluoroxypyr esters |
| butylate | |
| carbetamide | |
| chlornitrofen | |
| chlorpropham | |
| cinmethylin | |
| clethodim | |
| clomazone | |
| clopyralid esters | |
| CMPP esters | |
| cycloate | |
| cycloxydim | |
| desmedipham | |
| dichlorprop esters | |
| flurecol butyl | |
| flurochloralin haloxyfop | |
| ethoxyethyl | |
| haloxyfop-methyl | |
| ioxynil esters | |
| isopropalin | |
| MCPA esters | |
| mecoprop-P esters | |
| metolachlor | |
| monalide | |
| napropamide | |
| nitrofen | |
| oxadiazon | |
| oxyfluorfen | |
| pendimethalin | |
| phenisopham | |
| phenmedipham | |
| picloram esters | |
| pretilachlor | |
| profluralin | |
| propachlor | |
| propanil | |
| propaquizafop | |
| pyridate | |
| quizalofop-P | |
| triclopyr esters | |
| tridiphane | |
| trifluralin | |

Other pesticides such as the nitrification inhibitor nitrapyrin may also be employed. The compositions of the invention may also incorporate mixtures of two or more pesticides.

The pesticide may be an organosoluble derivative of a pesticidal compound which is itself poorly organosoluble or insoluble.

The aqueous phase may additionally comprise one or more water-soluble pesticidal components.

The compositions in accordance with the invention may also include an additional solid phase dispersed in the aqueous phase (so called suspension-emulsions).

Suspension-emulsions are recognised as formulations which are difficult to stabilise because of the tendency for unfavourable interactions between oil droplets and solid particles in the formulation and also between mulsifiers and the dispersing agents used to suspend the solid component, very often leading to premature breakdown of the formulation.

By the preparation of suspension-emulsions as compositions in accordance with the invention, employing a stabilizer of the kind described above, together with an appropriate aqueous dispersing agent for the solid suspended phase, it is possible to control or eliminate crystal growth of the solid dispersed pesticide. With is certain types of suspension emulsion, where the dispersed solid has an appreciable solubility in the dispersed liquid phase, this has hitherto been difficult to achieve.

Aqueous dispersing agents for such dispersed solids are well known to those skilled in the art and include nonionic surfactants such as ethylene oxide/propylene oxide block copolymers, polyvinyl alcohol/polyvinyl acetate copolymers, polymeric nonionic surfactants such as the acrylic graft copolymers.

Anionic surfactants suitable as dispersing agents include polyacrylates, lignosulphonates, polystyrene sulphonates, maleic anhydride-methyl vinyl ether copolymers, naphthalene sulphonic acid formaldehyde condensates, phosphate ester surfactants such as a tristyrenated phenol ethoxylate phosphate ester, maleic anhydride-diisobutylene copolymers, anionically modified polyvinyl alcohol/polyvinylacetate copolymers, and ether sulphate surfactants derived from the corresponding alkoxylated nonionic surfactants. Preferred aqueous dispersing agents are the class of polymeric surfactants described in UK Patent Soecifications Nos 2026341A and 1196248.

A particularly preferred dispersing agent is an acrylic graft copolymer with nonionic surface active properties, particularly those of the type known as "comb" surfactants, and in particular surfactants of the type sold under the Trade Mark ATLOX 4913, which contains about 36.6% methylmethacrylate, 1.9% methacrvlic acid, both grafted with methoxypoly(ethylene glycol) 750 methacrylate (61.5%). We have found that this surfactant can be added to the oil phase before preparation of the emulsion, to the emulsion before addition to the suspension concentrate, to the mill-base before milling of the suspension concentrate, to the post-mill concentrate after milling or to the emulsion/suspension concentrate mix as a final addition.

Pesticides which may be formulated as the solid phase of such a suspension concentrate are well known in the art and are extensively exemplified in "The Pesticide Manual" 9th Edition, Ed. C R Worthing & R J Hance. Such pesticides are characterised by relatively high melting points (usually above 70° C.) and low water solubility (usually less than 200 ppm) although exceptions can be found to this generalisation. They include the triazine herbicides, such as atrazine, urea herbicides such as isproturon, insect growth regulator insecticides such as the acyl ureas, exemplified by hexaflumuron, chlorinated hydrocarbon insecticides such as gamma-HCH, fungicides such as carbendazim, captan, maneb, chlorothalonil, thiophanatemethyl, some ergosterol biosynthesis inhibitor fungicides such as flutriafol and dichlobutrazol and amide herbicides such as propyzamide and isoxaben.

The optional additional solid phase may also be a microcapsule suspension, offering the potential of either mixing pesticides for differing biological effects or a mixture of the same pesticide as an emulsion for immediate effect against its target organism with a microencapsulated presentation of that same pesticide -for a delayed-release effect.

The disperse (non-aqueous) phase may comprise a further internal aqueous phase.

The compositions of the invention may also include optional adjuvants such as freezing point depressants preferably in amounts of 0 to 15 percent, flow aids to prevent caking or aid in the re-dispersion of bottom sediment preferably in amounts 0 to 5 percent, thickening agents preferably in amounts of 0 to 3 percent, antibacterial agents preferably in amounts of from 0 to 2 percent, and defoamers preferably in amounts of 0 to 1 percent to improve the overall properties under field storage and use conditions.

Similarly, conventional pesticide additives such as adjuvants, surfactants for increasing penetration of the active substances or salts may be incorporated into the compositions to maintain or improve biological efficacy of the composition. These may be incorporated into the non-aqueous phase or aqueous phase as appropriate.

The invention is illustrated by the following Examples. The following list identifies the various starting materials used in the Examples:

| | Pesticides | Trade Mark |
|---|---|---|
| A | Chlorpyrifos 65% w/w solution in xylene | DURSBAN XM |
| B | Chlorpyrifos | DURSBAN F |
| C | Fluroxypyr BP | STARANE |
| D | Fenpropimorph | |
| E | 5,7-Dichloro-4-(4-Fluorophenoxy) Quinoline | |
| | Surfactants | |
| F | Ethoxylated alcohol | ATLOX 4991 |
| G | Ethyleneoxide/propyleneoxide block copolymer | PLURONIC PE 10500 |
| H | Polyvinyl alcohol | Gohsenol GH-23 |
| I | Acrylic graft copolymer | ATLOX 4913 |
| J | Polyvinyl alcohol | Gohsenol GL-03 |
| | Solvents | |
| K | Xylene | |
| L | Toluene | |
| M | Aromatic $C_9$–$C_{10}$ benzenoid distillate | SOLVESSO 150 |
| N | 1-methylnaphthalene | |
| O | Propyleneglycol mono-n-butyl ether | DOWANOL PnB |

| | Stabiliser | Trade Designation | Mol. Wt. |
|---|---|---|---|
| P | Polypropylene glycol | POLYGLYCOL P4000 | 4,000 |
| Q | Polyisobutene | HYVIS 04 | 350–400 |
| R | Polyisobutene | HYVIS 30 | 2,000–3,000 |
| S | Polyisobutene | HYVIS 2000 | 20,000 |
| T | Methyl oleate | | 296 |
| U | Polystyrene | | 250,000 |
| V | Polyoctadeylmethacrylate | | 180,000 |
| W | Polyvinylstearate | | 90,000 |
| X | Polyhydroxystearic acid PEG ester | ATLOX 4912 | 10,000 |
| B1 | Glyceryl trioleate | | 886 |
| C1 | a polydimethyl cyclosiloxane containing more than 90% dodecamethyl cyclohexa siloxane | DowCorning DC246 | 444 |
| D1 | alkyl modified poly-dimethylsiloxane with molecular weight approx 350 containing about 33% alkyl (as percentage of molecular weight) | AS-1 from OSI | 350 |
| E1 | alkyl modified poly-dimethylsiloxane with molecular weight approx. 2600 containing about 43% alkyl (as percentage of the molecular weight) | AS-3 from OSI | 2,600 |
| F1 | polybutylene oxide | DOW CHEMICAL Synalox OA-185 | 2,000 |
| G1 | polybutylene oxide | DOW CHEMICAL Synalox OA-90 | 1,500 |
| H1 | ethylcellulose, viscosity grade 7 | DOW CHEMICAL Ethocel S-7 | 64,000 |

GENERAL METHOD OF PREPARATION OF EXAMPLES 1–35

The non-aqueous phase was first prepared by dissolving the sabiliser in a solvent. The pesticide (when used) was added to the solvent/stabiliser solution. If no solvent was required (in the case of a liquid pesticide), the stabiliser was added directly to the liquid pesticide. This non-aqueous phase was then emulsified into an aqueous solution of surfactant with high shear mixing (Silverson) for about 30 seconds. Samples were stored at a range of temperatures for varying periods of time. Particle size analysis of samples was carried out by use of a Malvern Mastersizer using an appropriate presentation code for the refractive index of the non-aqueous phase in the respective test emulsion. Size data are reported in volume mean diameter (vmd) in microns and span (an indicator of the width of the distribution which is calculated according to $$\text{Span} = \frac{D(V, 0.9) - D(V, 0.1)}{D(V, 0.5)}$$

where D (V,P) is the diameter at the percentage point (0.9=90%, 0.1=10% and 0.5=50%). All units are grams.

TABLE 1

| Example | Pesticide | Solvent | Surfactant | Stabiliser | Water |
|---|---|---|---|---|---|
| 1 | None | L 50 | F 5.0 | None | 45 |
| 2 | None | L 47.5 | F 5.0 | U 2.5 | 45 |
| 3 | A 35.0 | M 15.0 | F 5.0 | None | 45 |
| 4 | A 35.0 | M 11.25 | F 5.0 | U 3.75 | 45 |
| 5 | B 48.0 | M 25.8 | F 5.0 | None | 32.4 |
| 6 | B 48.0 | M 22.0 | F 5.0 | U 3.8 | 32.4 |
| 7 | B 48.0 | L 15.8 | F 5.0 | V 10.0 | 32.4 |
| 8 | B 48.0 | M 23.5 | F 5.0 | W 2.3 | 32.4 |
| 9 | B 48.0 | M 20.6 | F 5.0 | None | 37.9 |
| 10 | B 48.0 | M 17.2 | F 5.0 | U 3.4 | 37.9 |
| 11 | B 48.0 | M 16.0 | F 5.0 | None | 47.5 |
| 12 | B 48.0 | M 12.8 | F 5.0 | U 3.2 | 47.5 |
| 13 | B 48.0 | M 22.1 | G 4.0 | U 3.7 | 33.4 |
| 14 | B 48.0 | M 24.0 | G 4.0 | U 1.85 | 33.4 |
| 15 | B 48.0 | M 30.0 | G 2.85<br>F 2.0 | U 2.0 | 26.2 |
| 16 | B 48.0 | M 25.8 | G 4.0 | None | 33.4 |
| 17 | B 48.0 | M 25.8 | G 4.0 | P 7.4 | 33.4 |
| 18 | B 48.0 | M 25.8 | G 4.0 | R 3.7 | 33.4 |
| 19 | B 48.0 | M 25.8 | G 4.0 | U 0.74 | 33.4 |
| 20 | C 53.0 | O 5.0 | G 2.0<br>O 0.5 | None | 53.0 |
| 21 | C 53.0 | None | G 2.0<br>H 0.5 | P 5.0 | 53.0 |

TABLE 1-continued

| Example | Pesticide | Solvent | Surfactant | Stabiliser | Water |
|---|---|---|---|---|---|
| 22 | C 53.0 | None | G 2.0<br>H 0.5 | P 1.0<br>T 4.0 | 53.0 |
| 23 | C 53.0 | None | G 2.0<br>H 0.5 | T 4.0<br>X 1.0 | 53.0 |
| 24 | D 52.0 | None | H 0.5<br>G 2.0 | None | 42.0 |
| 25 | D 52.0 | None | G 2.0<br>H 0.5 | P 5.0 | 4 |
| 26 | None | L 60.0 | F 4.0 | None | 36.0 |
| 27 | None | L 60.0 | G 4.0 | None | 36.0 |
| 28 | None | L 57.0 | F 4.0 | Q 3.0 | 36.0 |
| 29 | None | L 57.0 | G 4.0 | Q 3.0 | 36.0 |
| 30 | None | L 57.0 | F 4.0 | R 3.0 | 36.0 |
| 31 | None | L 57.0 | G 4.0 | R 3.0 | 36.0 |
| 32 | None | L 57.0 | F 4.0 | P 3.0 | 36.0 |
| 33 | None | L 57.0 | G 4.0 | P 3.0 | 36.0 |
| 34 | None | L 57.0 | F 4.0 | T 3.0 | 36.0 |
| 35 | None | L 57.0 | G 4.0 | N 3.0 | 36.0 |

The particle size (in micrometers) and particle size span of the formulations were evaluated after storage of the formulations at a range of times and temperatures. The results are given in table 2.

TABLE II

| Example | Storage Time (days) | Temp (° C.) | vmd (microns) | Span |
|---|---|---|---|---|
| 1 | initial | 20 | 0.70 | 8.65 |
| 1 | 28 | 20 | 9.0 | 1.60 |
| 1 | 210 | 20 | 21.19 | 1.46 |
| 2 | initial | 20 | 0.64 | 1.64 |
| 2 | 28 | 20 | 0.68 | 1.44 |
| 2 | 210 | 20 | 0.66 | 1.49 |
| 3 | initial | 20 | 1.53 | 0.98 |
| 3 | 21 | 20 | 7.40 | 1.46 |
| 3 | 210 | 20 | 20.73 | 1.34 |
| 3 | 330 | 20 | 25.62 | 1.56 |
| 4 | initial | 20 | 1.84 | 3.42 |
| 4 | 21 | 20 | 1.72 | 3.68 |
| 4 | 210 | 20 | 1.73 | 3.53 |
| 4 | 330 | 20 | 1.88 | 3.38 |
| 5 | initial | 20 | 1.78 | 1.37 |
| 5 | 28 | 20 | 10.08 | 1.42 |
| 6 | initial | 20 | 0.79 | 4.41 |
| 6 | 28 | 20 | 0.78 | 4.48 |
| 7 | initial | 20 | 1.18 | 1.83 |
| 7 | 28 | 20 | 1.18 | 1.85 |
| 8 | initial | 20 | 1.03 | 1.20 |
| 8 | 28 | 20 | 1.06 | 1.59 |
| 9 | initial | 20 | 1.09 | 1.13 |
| 9 | 28 | 20 | 8.28 | 1.74 |
| 10 | initial | 20 | 0.87 | 5.12 |
| 10 | 28 | 20 | 0.87 | 5.38 |
| 11 | initial | 20 | 1.29 | 1.27 |
| 11 | 28 | 20 | 10.05 | 1.30 |
| 12 | initial | 20 | 0.97 | 5.18 |
| 12 | 28 | 20 | 0.93 | 6.07 |
| 13 | 14 | −10 | 1.50 | 2.12 |
| 13 | 14 | 40 | 1.50 | 1.97 |
| 13 | 14 | 55 | 1.47 | 2.00 |
| 13 | 210 | 20 | 1.46 | 1.91 |
| 13 | 330 | 20 | 1.48 | 1.91 |
| 14 | initial | 20 | 1.56 | 1.47 |
| 14 | 14 | −10 | 1.62 | 1.51 |
| 14 | 14 | 40 | 1.54 | 1.34 |
| 14 | 14 | 55 | 1.41 | 1.43 |
| 14 | 210 | 20 | 1.50 | 1.46 |
| 14 | 330 | 20 | 1.51 | 1.44 |
| 26 | initial | 20 | 0.79 | 2.50 |
| 26 | 14 | −10 | 20.12 | 1.09 |
| 26 | 14 | 20 | 23.15 | 1.30 |
| 26 | 14 | −5/30 | 21.91 | 1.28 |

TABLE II-continued

| Example | Storage Time (days) | Temp (° C.) | vmd (microns) | Span |
|---|---|---|---|---|
| 26 | 14 | 40 | 20.01 | 1.38 |
| 26 | 180 | 20 | 26.84 | 1.30 |
| 27 | initial | 20 | 2.88 | 2.05 |
| 27 | 14 | −10 | 30.87 | 1.07 |
| 27 | 14 | 20 | 16.92 | 1.06 |
| 27 | 14 | −5/30 | 18.85 | 1.03 |
| 27 | 14 | 40 | 17.19 | 1.40 |
| 27 | 180 | 20 | 14.16 | 1.39 |
| 28 | initial | 20 | 0.39 | 1.15 |
| 28 | 14 | 20 | 0.40 | 1.18 |
| 28 | 14 | −5/30 | 0.40 | 1.16 |
| 28 | 14 | 40 | 0.39 | 1.46 |
| 28 | 180 | 20 | 0.40 | 1.20 |
| 28 | 300 | 20 | 0.36 | 1.23 |
| 29 | initial | 20 | 1.03 | 1.23 |
| 29 | 14 | 20 | 1.01 | 1.30 |
| 29 | 14 | −5/30 | 1.03 | 1.29 |
| 29 | 14 | 40 | 1.03 | 1.34 |
| 29 | 180 | 20 | 0.92 | 1.18 |
| 30 | initial | 20 | 0.38 | 1.16 |
| 30 | 14 | 20 | 0.39 | 1.16 |
| 30 | 14 | −5/30 | 0.38 | 1.14 |
| 30 | 14 | 40 | 0.37 | 1.30 |
| 30 | 180 | 20 | 0.37 | 1.13 |
| 30 | 300 | 20 | 0.34 | 1.21 |
| 31 | initial | 20 | 0.94 | 1.23 |
| 31 | 14 | 20 | 0.94 | 1.44 |
| 31 | 14 | −5/30 | 0.95 | 1.25 |
| 31 | 14 | 40 | 0.96 | 1.39 |
| 31 | 180 | 20 | 0.90 | 1.44 |
| 32 | initial | 20 | 0.38 | 1.16 |
| 32 | 14 | 20 | 0.38 | 1.17 |
| 32 | 14 | −5/30 | 0.37 | 1.12 |
| 32 | 14 | 40 | 0.36 | 1.65 |
| 32 | 180 | 20 | 0.36 | 1.25 |
| 32 | 300 | 20 | 0.33 | 1.43 |
| 33 | initial | 20 | 0.60 | 1.48 |
| 33 | 14 | −10 | 0.70 | 1.43 |
| 15 | initial | 20 | 0.92 | 1.75 |
| 15 | 14 | −10 | 0.89 | 2.34 |
| 15 | 14 | 40 | 0.87 | 1.45 |
| 15 | 14 | 55 | 0.87 | 1.38 |
| 15 | 210 | 20 | 0.82 | 1.82 |
| 15 | 330 | 20 | 0.87 | 1.57 |
| 16 | initial | 20 | 1.03 | 1.09 |
| 16 | 24 | −10 | 1.83 | 1.65 |
| 16 | 24 | 40 | 1.41 | 4.46 |
| 16 | 24 | 55 | 1.25 | 2.11 |
| 16 | 210 | 20 | 5.11 | 3.90 |
| 16 | 330 | 20 | 4.69 | 2.95 |
| 17 | initial | 20 | 1.13 | 1.05 |
| 17 | 24 | −10 | 1.13 | 1.08 |
| 17 | 24 | 40 | 1.19 | 1.04 |
| 17 | 24 | 55 | 1.18 | 1.13 |
| 17 | 210 | 20 | 1.12 | 1.00 |
| 17 | 330 | 20 | 1.00 | 1.00 |
| 18 | initial | 20 | 0.98 | 1.11 |
| 18 | 24 | −10 | 1.02 | 1.34 |
| 18 | 24 | 40 | 0.99 | 1.12 |
| 18 | 24 | 55 | 0.94 | 1.30 |
| 18 | 210 | 20 | 0.96 | 1.07 |
| 18 | 330 | 20 | 0.97 | 1.04 |
| 19 | initial | 20 | 2.19 | 1.54 |
| 19 | 24 | −10 | 2.21 | 1.74 |
| 19 | 24 | 40 | 2.04 | 1.78 |
| 19 | 24 | 55 | 1.89 | 1.28 |
| 20 | initial | 20 | 1.35 | — |
| 20 | 30 | 20 | 1.62 | — |
| 21 | initial | 20 | 1.65 | — |
| 21 | 30 | 20 | 1.65 | — |
| 22 | initial | 20 | 1.60 | — |
| 22 | 30 | 20 | 1.66 | — |
| 23 | initial | 20 | 1.60 | — |
| 23 | 30 | 20 | 1.64 | — |
| 24 | initial | 20 | 2.30 | — |
| 24 | 14 | 55 | 2.81 | — |

TABLE II-continued

| Example | Storage Time (days) | Temp (° C.) | vmd (microns) | Span |
|---|---|---|---|---|
| 25 | initial | 20 | 1.60 | — |
| 25 | 14 | 55 | 1.61 | — |
| 33 | 14 | 20 | 0.61 | 1.51 |
| 33 | 14 | −5/30 | 0.70 | 1.49 |
| 33 | 14 | 40 | 0.70 | 1.46 |
| 33 | 180 | 20 | 0.66 | 1.43 |
| 34 | initial | 20 | 0.41 | 1.16 |
| 34 | 14 | 20 | 0.42 | 1.28 |
| 34 | 14 | −5/30 | 0.42 | 1.27 |
| 34 | 14 | 40 | 0.43 | 1.76 |
| 35 | initial | 20 | 0.95 | 1.17 |
| 35 | 14 | −10 | 0.97 | 1.18 |
| 35 | 14 | 20 | 0.95 | 1.19 |
| 35 | 14 | −5/30 | 0.98 | 1.19 |
| 35 | 14 | 40 | 1.05 | 1.17 |
| 35 | 180 | 20 | 0.90 | 1.32 |

References to a temperature of −5/30 indicate that the sample was subjected to a 12 hour temperature cycle between these temperatures.

Examples 1, 3, 5, 9, 11, 16, 20, 24, 26 and 27 which are comparative because they do not include stabiliser show the typical increase in size with time ranging from greater than a 20% relative increase in vmd to over a 30 fold increase, dependent upon storage regime and sample type.

Examples of the invention reduce the increase in size to less than 10%. Often no change in size or span is seen within the error of the measurement methodology.

EXAMPLE 36

An emulsion containing stabiliser R was prepared by adding a solution of stabiliser R (24 g) and solvent N (24 g) to water (27 g) containing surfactant F (5 g). This was emulsified to produce an emulsion with a particle size-vmd-of 0.73 microns. This was labelled sample S1.

10 g of this emulsion was then taken and added to water (37 g) with surfactant F (3 g). Pesticide A (50 g) was then added to the diluted emulsion and mixed lightly. Allowing to stand for 30 minutes and measuring the particle size gave a figure of 1.44 microns. After 6 hours the number had changed to 1.50 microns. The calculated value if all the added material had combined with the particles of emulsion S1 was 1.46 microns. The product remained at that size.

This constituted the addition of 7 volumes of non-aqueous material (referred to hereinafter simply as "oil" for simplicity) to one volume of non-mobile emulsion. This was labelled Sample S2.

EXAMPLE 37

A 60% v/v emulsion of pesticide A in water was prepared by adding 70.8 g Pesticide A to water (30 g) and surfactant F (5 g). This was emulsified to produce an emulsion of particle size-vmd-of 0.57 microns. This was labelled Sample S3.

Aliquots of S2 and S3 were mixed in the following ratios and allowed to equilibrate over a weekend. The particle sizes were measured and compared to a calculated value assuming all the added mobile emulsion (S3) migrated to the non-mobile emulsion (S2).

TABLE III

| S2 oil volume | S3 oil volume | vmd found | vmd calculated |
|---|---|---|---|
| 1 | 1 | 1.83 | 1.81 |
| 1 | 2 | 2.04 | 2.07 |
| 1 | 3 | 2.22 | 2.29 |
| 1 | 5 | 2.52 | 2.62 |
| 1 | 7 | 2.74 | 2.88 |
| 1 | 10 | 3.24 | 3.20 |

Over this period the emulsion without any non-mobile phase (S3) ripened to 3.96 microns whilst the intermediate emulsion S2) remained at 1.50 microns. The 1:10 volume figure equates to 70 volumes oil added to the initial emulsion (S1). Since that emulsion only contains 50% non-mobile phase in the non-aqueous phase, the final figure actually equates to the addition of 140 volumes mobile oil to a non-mobile component—which equates to a non-mobile component content of 0.7% in the non-aqueous phase of the emulsion.

EXAMPLE 38

A solution of Stabiliser S (25 g) in Solvesso 200(TM) (a mixed methyl naphthalene solvent) (25 g) was emulsified into water (45 g) with Surfactant F (5 g). This gave an emulsion with a particle size-vmd-of 5.77 microns. The sample was labelled S4.

An emulsion of pesticide A was prepared by emulsifying Pesticide A (60 g) into water (35 g) and surfactant F (5 g). This had a particle size of 0.84 microns and was labelled S5.

Aliquots of S4 and S5 were mixed in the amounts 10 g:50 g respectively and left to equilibrate.

Over a weekend storage, the particle sizes were then measured as follows:

| −S4 | −S5 | mix of S4 + S5 |
|---|---|---|
| 5.77 | 2.55 | 10.09 |

The calculated value if all the mobile phase had migrated to the non-mobile emulsion was 10.38 microns. The value for the emulsion alone (2.55) indicates that the emulsion could not have ripened to such a large size (10.09) of its own accord in the time period.

EXAMPLE 39

Technical molten pesticide B at 50° C. (61 g) was added to water (34 g) and surfactant F (5 g) at 50° C. and shaken to produce a very coarse emulsion. To this was added a previously prepared emulsion labelled S1 (see above) (20 g). The mix was allowed to stand for 30 minutes and then measured for particle size.

| found | calculated |
|---|---|
| 1.20 | 1.21 |

This supersaturated emulsion was then allowed to stand for about 10 days after which time the excess pesticide B had extensively crystallised. Warming this very non-homogeneous mix to 45° C. and allowing to stand for a further 30 minutes again gave an emulsion which was measured for particle size. This was found to be 1.18 microns. This is very close to the original figure of 1.20 microns. This demonstrates the ability of this system to recover a size distribution when a non-mobile component is present in the formulation.

EXAMPLE 40

An emulsion was prepared with solvent N containing 5% relative stabiliser R. This had a particle size of 1.23 microns. A second emulsion was prepared with solvent N containing 50% relative stabiliser R. This had a particle size of 1.57 microns. These were then mixed in equal amounts and allowed to equilibrate. It was observed that the mobile oil migrated from the 5% relative stabiliser R emulsion to the 50% relative emulsion, producing a bimodal distribution as the 1.23 micron emulsion reduced and 1.57 micron emulsion swelled. This contrasted strongly with the calculated size and particle size distribution for a simple mixing without interaction of the two emulsions.

STORAGE OF EMULSIONS FROM EXAMPLE 37

The emulsions from Example 37 were stored for extended periods of time and their sizes measured. The data are presented in Table IV.

TABLE IV

| S2 | S3 | vmd | vmd found after | | |
|---|---|---|---|---|---|
| oil vol | oil vol | calc | 1 day | 180 days | 300 days |
| 1 | 1 | 1.81 | 1.83 | 1.80 | 1.81 |
| 1 | 2 | 2.07 | 2.04 | 2.02 | 2.02 |
| 1 | 3 | 2.29 | 2.22 | 2.23 | 2.19 |
| 1 | 5 | 2.62 | 2.52 | 2.49 | 2.47 |
| 1 | 7 | 2.88 | 2.74 | 2.71 | 2.73 |
| 1 | 10 | 3.20 | 3.24 | 3.19 | 3.14 |
| 1 | 0 | 1.46 | 1.50 | 1.46 | 1.47 |
| 0 | 1 | — | 0.57 | 20.84 | 21.56 |

These data again illustrate the typical instability of an emulsion without the addition of a suitable stabiliser and again illustrate the products of the current invention which have superior stability. These Examples 36–40 also illustrate other aspects of the current invention, especially the ability to add large volumes of non-aqueous phase to a template emulsion, thereby producing a resultant stable emulsion in an entirely predictable manner.

PREPARATION OF STABLE SUSPO-EMULSIONS (SE'S)

The preparation and stability of the emulsions used in the preparation of suspo-emulsions is described in examples 41–45. The preparation and stability of suspo-emulsions is described in examples 46–52. (Particle size data is given in the tables).

(a) Emulsion Phase Preparation

EXAMPLE 41

An emulsion containing stabiliser Q was prepared by adding a mixture of pesticide D (250 g) and stabiliser Q (25 g) to water (175 g) containing propylene glycol (25 g) and surfactant F (25 g). High shear was employed. The sample is referred to as S41.

EXAMPLE 42

An emulsion was prepared by adding pesticide D (250 g) to water (204.5) containing surfactant H (5 g), surfactant G (15 g), propylene glycol (25 g) and silicone antifoaming agent (Trade Mark Foamaster UDB) (0.5 g). High shear was employed. The sample is referred to as S42.

EXAMPLE 43

An emulsion was prepared by adding pesticide D (250 g) to water (192 g) propylene alycol (25 g), Foamaster UDB (5 g) and surfactant F (25 g) under high shear. The sample is referred to as S43. The particle size was measured initially as 1.29 microns vmd and after 22 days had approximately doubled in size.

EXAMPLE 44

An emulsion was prepared by adding a mixture of pesticide D (250 g) and stabiliser Q (75 g), to water (224.5 g), surfactant J (25 g), Foamaster UDB (0.5 g) and propylene glycol (25 g). The sample is referred to as S44.

EXAMPLE 45

An emulsion was prepared by adding pesticide D (250 g) to water (299.5 g), surfactant J (25 g), Foamaster UDB (0.5 g) and propylene glycol (25 g). The sample is referred to as S45.

(b) Suspo-emulsion Preparation

To illustrate the claimed invention microscope data is presented (see attached table) as evidence of occurrence, or not, of crystal growth. Particle size data is available but the high phase volume ratio of oil droplets compared to solid disperse phase effectively hides (by dilution) the solid disperse phase particle size distribution.

EXAMPLE 46

Pesticide E (67 g) was bead milled with an anionic surfactant (Trade Mark Morwet D425) (2.7 g), Foamaster UDB (0.2 g), microcystalline cellulose viscosity modifier (Trade Mark Avicel CL611 (0.4 g) and water (41.2 g). The sample is referred to as S46. Particle size of the suspension concentrate thus formed is given in the table.

EXAMPLE 47

To S46 (111.2 g) was added S41 (500 g), Keizan S (1 g), Proxel GXL (0.5 g), Avicel CL611 (9.7 g) and water (347.6 g) and mixed with a medium shear mixer.

EXAMPLE 48

To S46 (111.2 g) was added surfactant I (50 g), S41 (500 g), heteropolysaccharide gum viscosity modifier (Trade Mark Kelzan S) (1 g), a biocide (Trade Mark Proxel GXL) (0.5 g), Avicel CL611 (9.7 g) and water (297.6 g) and mixed with a medium shear mixer.

EXAMPLE 49

To S46 (111.2 g) was added surfactant I (50 g), S42 (500 g), Keizan S (1 g), Proxel GXL (0.5 g), Avicel CL611 (9.7 g) and water (297.6 g) and mixed with a medium shear mixer.

EXAMPLE 50

To S46 (111.2 g) was added S43 (500 g)) and mixed with a medium shear mixer.

EXAMPLE 51

To S46 (111.2 g) was added S44 (600 g), Kelzan S (1 g), Proxel GXL (0.5 g), Avicel CL611 (9.7 g) and water (277.8 g) and mixed with a medium shear mixer.

EXAMPLE 52

To S46 (111.2 g) was added S45 (600 g), Kelzan S (1 g), Proxel GXL (0.5 g), Avicel CL611 (9.7 g) and water (277.8 g) and mixed with a medium shear mixer.

EXAMPLE 53

To S46 (111.2 g) was added S44 (600 g), Kelzan S (1 g), Proxel GXL (0.5 g), Avicel CL611 (9.7 g) and water (277.8 g) and mixed with a medium shear mixer.

TABLE V

Results of particle size evaluations after storage of emulsion phases and suspension concentrate at a range of times and temperatures

| Example | Time of Storage (days) | Storage Temp (° C.) | vmd (microns) | Span |
|---|---|---|---|---|
| 41 | Initial | 20 | 1.05 | 0.98 |
| 41 | 21 days | −5/+30 | 1.04 | 0.94 |
| 41 | 21 days | 20 | 1.07 | 0.83 |
| 41 | 21 days | 55 | 1.20 | 0.93 |
| 42 | Initial | 20 | 0.94 | 0.95 |
| 42 | 82 days | 20 | 7.35 | 2.03 |
| 44 | Initial | 20 | 1.82 | 1.14 |
| 44 | 22 days | 20 | 1.83 | 1.09 |
| 45 | Initial | 20 | 3.71 | 1.92 |
| 45 | 22 days | 20 | 5.00 | 2.41 |
| 46 | Initial | 20 | 1.27 | 4.59 |
| 46 | 90 days | 20 | 1.18 | 4.83 |
| 46 | 90 days | 55 | 1.24 | 4.55 |

Data measured on Malvern Mastersizer, 45 mm lens, presentation code 0607 (Examples 41–45) and 0807 (Example 46).

These data confirm the stability of emulsions with stabiliser (Examples 41 and 44) and the stability of the suspension concentrate (Example 46). They also again demonstrate the instability of an emulsion without stabiliser (Examples 42 and 45).

TABLE VI

Microscope (X50 Magnification) evaluation of suspo-emulsion samples after storage at a range of times and temperatures

| Example | Storage time days | Storage temp (° C.) 40 | −5/+30 |
|---|---|---|---|
| 47 | 28 | Crystals > 100 μm | |
| 48 | 28 | No growth | |
| 49 | 28 | 10–30 μm new crystals | |
| 50 | 19 | Long needle crystals 30–50 μm | Long needle 30–50 μm |
| 51 | 9 | 10 μm crystals (new) | A few crystals 10–20 μm. Growth |
| 52 | 9 | Some growth (<10 μm) | Some growth (<10 μm) |
| 53 | 9 | No growth | No growth |

(NB. Initial solid disperse phase particle size was as for sample S46 (ie. 1.27 μm vmd, span 4.59)

It can be seen that both stabiliser and Atlox 4913 are necessary to control crystal growth (Example 48)—in the absence of either stabiliser (Example 49) or Atlox 4913 (Example 47) or both (Example 50) crystal growth still occurs. Using a different emulsifier in the emulsion phase the same effect is shown by examples 51, 52 and 53 (stabiliser only, Atlox 4913 only, stabiliser + Atlox 4913 respectively).

(NB. No crystal growth occurs in the absence of emulsion phase (Example 46)).

EXAMPLES 54 TO 62

The efficacy of stabilisers S1 to H1 was established, in comparison with stabiliser Q above, by the following tests. Stabiliser A, and stabilisers B1 to G1 were added to toluene so as to produce a solution containing 5% of the stabiliser in toluene. Similarly, a 10% solution of stabiliser H1 was formed with toluene. This non-aqueous phase was then emulsified as in the general preparation method described above, into a solution containing a detergent (Atlox 4991) in water, so as to produce formulations having the composition indicated in Table VII. The particle sizes of the resulting emulsions were measured as above, and the variation in particle size on storage was also determined. The results are shown in Table VIII.

TABLE VII

| Example | Stabiliser | Stabiliser % | Toluene % | Atlox 4991% | Water % |
|---|---|---|---|---|---|
| 54 | none | — | 50.0 | 5 | 45.0 |
| 55 | A1 | 2.5 | 47.5 | 5 | 45.0 |
| 56 | B1 | 2.5 | 47.5 | 5 | 45.0 |
| 57 | C1 | 2.5 | 47.5 | 5 | 45.0 |
| 58 | D1 | 2.5 | 47.5 | 5 | 45.0 |
| 59 | E1 | 2.5 | 47.5 | 5 | 45.0 |
| 60 | F1 | 2.5 | 47.5 | 5 | 45.0 |
| 61 | G1 | 2.5 | 47.5 | 5 | 45.0 |
| 62 | H1 | 5.0 | 45.0 | 5 | 45.0 |

TABLE VIII

| Example | Storage Time (days) | Temp (° C.) | vmd (microns) |
|---|---|---|---|
| 54 | Initial | — | 2.94 |
| | 5 | 20 | 8.55 |
| | 5 | 40 | 9.29 |
| | 85 | 20 | 9.52 |
| 55 | Initial | — | 0.37 |
| | 5 | 20 | 0.37 |
| | 5 | 40 | 0.32 |
| | 85 | 20 | 0.33 |
| 56 | Initial | — | 0.36 |
| | 5 | 20 | 0.37 |
| | 5 | 40 | 0.32 |
| | 85 | 20 | 0.33 |
| 57 | Initial | — | 0.38 |
| | 5 | 20 | 0.35 |
| | 85 | 40 | 0.36 |
| | 85 | 20 | 0.39 |
| 58 | Initial | — | 0.38 |
| | 5 | 20 | 0.36 |
| | 5 | 40 | 0.35 |
| | 85 | 20 | 0.35 |
| 59 | Initial | — | 0.35 |
| | 5 | 20 | 0.33 |
| | 5 | 40 | 0.33 |
| | 85 | 20 | 0.34 |
| 60 | Initial | — | 0.36 |
| | 5 | 20 | 0.36 |
| | 5 | 40 | 0.31 |
| | 85 | 20 | 0.31 |
| 61 | Initial | — | 0.36 |
| | 5 | 20 | 0.36 |
| | 5 | 40 | 0.30 |
| | 85 | 20 | 0.33 |

TABLE VIII-continued

| Example | Storage Time (days) | Temp (° C.) | vmd (microns) |
|---|---|---|---|
| 62 | Initial | — | 0.59 |
| | 11 | 20 | 0.63 |
| | 11 | 40 | 0.59 |
| | 85 | 20 | 0.56 |

EXAMPLE 63

A template emulsion was prepared by emulsifying stabiliser D1 above (60 g) into a solution of surfactant F (10 g) in water (50 g). This sample was coded A. A 20 g aliquot of this sample A was diluted with water (25 g) and 50 g of a 50% solution of chiorpyrifos in xylene added thereto. This sample was coded B. A further 20 g aliquot of sample A was diluted with water (25 g) and surfactant F (2 g) and 53 g of fenpropimorph added thereto. This sample was coded C.

Samples A, B, & C were stored and evaluated for changes in particle size. The results are shown in Table IX

TABLE IX

| Sample | Storage Time (days) | Temp (° C.) | vmd (microns) |
|---|---|---|---|
| A | initial | — | 0.43 |
| | 6 | 20 | 0.42 |
| | 85 | 20 | 0.44 |
| B | initial | — | 0.69 |
| | 6 | 20 | 0.69 |
| | 85 | 20 | 0.70 |
| C | initial | — | 0.86 |
| | 6 | 20 | 0.88 |
| | 85 | 20 | 0.93 |

EXAMPLE 64

An ethylcellulose dispersion (Tm Aauacoat) (30 g) was diluted with surfactant F and water (16 g). 50 g of a 65% chlorpyrifos solution in xylene was added thereto. The sample was coded D and stored at ambient temperature and evaluated for changes in particle size. The results are as follows

| Sample | Storage Time (days) | Temp (° C.) | vmd (microns) |
|---|---|---|---|
| D | initial | — | 0.35 |
| | 2 | 20 | 0.37 |
| | 21 | 20 | 0.37 |

Example 63 and 64 indicate that it is possible to take a previously prepared template (also stable to storage) and add a non-aqueous phase thereto to produce a stable emulsion without the need for high speed shear mixing procedures.

This method can be employed whether the addition of the non-aqueous material is made as a bulk addition, or by addition to the template emulsion of a second emulsion containing the further non-aqueous material in dispersed form. The method thus gives the ability to control the particle size of a diluted emulsion by addition of a template. This opens the possibility of improving the general field performance of diluted emulsifiable concentrate sprays by stabilising the emulsion size. It also makes it possible to improve (i.e., to narrow) the particle size distribution of existing emulsion preparations, for example commercial pesticidal emulsion preparations) by the addition of suitable template emulsions thereto.

EXAMPLE 65

Commercial emulsifiable concentrate (EC) formulations were diluted into laboratory tap water to product 1% v/v emulsions and the particle size measured after one hour.

In a parallel study, the EC formulations were diluted in the same manner and then an equivalent amount of the template emulsion referred to as sample A in Example 63 added thereto and the particle size measured after one hour. The results are shown in Table X.

TABLE X

| Sample | Template added | Particle Size vmd (microns) |
|---|---|---|
| STARANE 2 | – | 27.65 |
| STARANE 2 | + | 0.53 |
| TREFLAN 4 | – | 12.18 |
| TREFLAN 4 | + | 0.53 |
| DURSBAN 4 | – | 6.43 |
| DURSBAN 4 | + | 0.49 |
| DURSBAN 220E | – | 0.40 |
| DURSBAN 220E | + | 0.50 |

In another experiment a template was prepared by mixing a polyisobutene with a molecular weight of 400 (Hyvis 05–42 g) stabiliser F1 (18 g) and glyceryl trioleate (40 g). 50 g of this oil mixture was emulsified into surfactant F (9 g), an anionic surfactant (Anonaid HF) (5 g) and water (36 g). This template was then added to diluted EC's as above and the particle sizes measured. The resulting particle sizes were as follows:

| Template | Pesticide | Particle Size vmd (microns) |
|---|---|---|
| + | TREFLAN 4 | 0.43 |
| + | STARANE 2 | 0.42 |
| + | NONE | 0.38 |

All these examples illustrate the utility of being able to control the particle size of diluted emulsions in a spray tank by use of a template emulsion as a spray tank additive.

The production of emulsions with narrow particle size distributions opens a variety of possibilities in the field of microencapsulation. Two important methods of microencapsulation are:

a) interfacial polymerisation, and b) coacervation.

Both techniques involve the preparation of an oil-in-water emulsion, followed by either a condensation reaction that the oil/water interface to produce a polymeric film, or the production of a coacervate which can then deposit on the oil surface, followed by film forming and hardening, which can take place by a variety of processes. The condensation reaction can for example be a multi-component reaction between, for example acid chlorides and polyamines isocyanates and polyamines, isocyanates and polyols, or mixtures of the above.

Coacervates can be formed by many of the processes taught in the art, for example using gelatine/gum arabic.

The capsules formed by these processes can be effected by:

a) emulsion size b) a ratio of polymer/reactants/oil phase c) type and speed of encapsulation reaction.

Specifically, the wall thickness of the capsules is dependent upon the surface area of the preformed emulsion, and the ratio of the oil phase to the reactants capable of forming the polymer film.

By employing the method of the invention, utilising a stabiliser which is not transportable through the aqueous phase, it is possible to prepare initial emulsions with consistently reproducible particle size, and, more importantly, particle size distribution. These characteristics of the initial emulsion are carried through to the resulting microcapsules, enabling the production of encapsulated materials which, in turn, have reproducible particle size and particle size distribution.

Such microcapsules may be produced utilising the preferred stabilisers having a molecular weight not more than $10^4$, but may also be produced using the stabilisers disclosed for example in EP-A-0589838.

EXAMPLE 66

A template emulsion was prepared by emulsifying stabiliser F1 (40 g) into a solution of surfactant F(12 g) in water (48 g). This sample was coded A. the particle size of this product was 2.35 microns vmd. A 62.5 g aliquot of this sample A was taken and thereto added a mixture of 24 g of a 65% w/w solution of chlorpyrifos in xylene and 1 g of Voranate M-220 (a polyisocyanate). The mixture was shaken, left for five minutes and then diluted with 50 g water. To the dispersion was then added 0.3 g diethylenetriamine in 9.7 g water to effect the polycondensation and produce a microcapsule product. The microcapsules were clearly visible under an optical microscope. The particle size was measured and found to be 2.82 microns vmd. The calculated value for all the oil adding to the template in a controlled manner was also 2.82 microns vmd.

EXAMPLE 67

Samples of the product from Example 37 were treated with a polyisocyanate and then encapsulated by addition of amine to effect a condensation. The results were as tabulated below employing the general recipe:

Stable emulsion from Example 37 100 g

Polyisocyanate (Voranate M-220) 1 g

Xylene (to dilute polyisocyanate) 1 g

Mixture shaken and allowed to equilibrate for 5 minutes. Water (50 g) added then diethylenetramine (0.3 g) in water (9.7 g) to effect a condensation and produce the microcapsule product.

TABLE XI

| Products from Example 37 | | |
|---|---|---|
| Initial Particle Size vmd | Capsule vmd (all in microns) | Calculated Capsule vmd |
| 1.50 | 1.57 | 1.52 |
| 1.81 | 1.85 | 1.83 |

A further capsule was prepared in a similar manner by taking a stable emulsion from Example 37 with a particle size of 2.19 microns (100 g) and adding toluene diisocynate (2 g) thereto and allowing to equilibrate for 5 minutes. Diethylene-triamine (0.6 g) in water (9.4 g) was added to effect a condensation and produce a microcapsule product. The particle size vmd was found to be 2.21 microns the calculated size was also 2.21 microns vmd.

The products of Example 67 demonstrate the ability to prepare an emulsion to any encapsulation procedure and then add a reactive polymer forming material as a last stage in the process, eliminating the need for long equilibration time (and potential for undesirable side reactions to occur).

EXAMPLE 68

A template emulsion was prepared by emulsifying a polyisobutene (Hyvis 05, molecular weight about 400) (20 g) with surfactant F (3 g) in water (50 g) containing a small amount (0.1 g) of anti foam agent (Antifoam UDB). The particle size of this product was 5.85 microns vmd.

A coacervation solution was prepared by taking a 5 g of 5% gelatin solution and 5 g of a gum arabic solution and diluting to 200 g with water. The pH was 8.43. This was warmed to 50° C.

A pesticidal oil was prepared by dissolving 166.7 g of Chlorpyrifos-methyl in 333.34 g of Solvesso 150 (an aromatic hydrocarbon). 10 g of this oil phase was added to 18.24 g of the previously prepared template and allowed to equilibrate. The particle size was found to be 9.3 microns.

This equilibrated emulsion (28.24 g) was added to the coacervation solution with gentle stirring. Th e pH after addition was 8.25, 2.95 g of a 2.5% acetic acid solution was added over 11 minutes to reduce the pH to 4.09. 1 g of a nonionic dispersant (Surfactant I) was added and the product cooled to below 10° C. over 7 minutes. Formaldehyde was then added (1 g) and the pH adjusted from 4.34 to 8.3 with dilute sodium hydroxide. The product was then an encapsulated pesticide with a particle size of 9.8 microns (some aggregation having taken place of the capsules).

It will be appreciated that the foregoing Examples are intended only as illustrations of compositions of the present invention, and that very many alternatives are possible within the scope of the appended claims.

In particular, although the compositions of the present invention are particularly suited for the formulation of pesticides, the invention can also be employed for the preparation of emulsions in a wide range of other industries, including the cosmetic, pharmaceutical, food, photographic, paint and polymer industries, and in the production of materials with controlled combustion properties. In a particular application, the ability to prepare emulsions with both particle size and particle size distribution which can be predicted accurately enables the production of pharmaceutical preparations for intravenous delivery, which can be targeted at particular organs, for example at the liver or kidneys, depending upon the particle size chosen. Other particular applications are in the preparation of emulsions which are stable in hostile environments such as high temperature and/or pressure, or in high electrolyte concentration.

What is claimed is:

1. A stable concentrated emulsion composition comprising a continuous aqueous phase and a discontinuous nonaqueous phase which discontinuous phase comprises a substance capable of transport through the aqueous phase to cause Ostwald ripening of the emulsion wherein the discontinuous phase further comprises a stabilizer that is soluble in the discontinuous phase, but less than 10 ppm soluble in and not transportable through the continuous phase and has a molecular weight of at least 250 to about 10,000, in an amount sufficient to diminish or prevent Ostwald ripening of the emulsion.

2. An emulsion as claimed in claim 1, wherein the discontinuous phase comprises a pesticidal material.

3. An emulsion as claimed in claim 1, which comprises a dispersing agent which is an ethylene oxide/propylene oxide block copolymers, a polyvinyl alcohol/polyvinyl acetate copolymer, an acrylic graft copolymer, a polyacrylate, a lignosuiphonate, a polystyrene sulphonate, a maleic anhydride-methyl vinyl ether copolymer, a naphthalene sulphonic acid formaldehyde condensate, a tristyrenated phenol ethoxylate phosphate ester, a maleic anhydride-diisobutylene copolymer or an ether sulphate surfactant.

4. An emulsion as claimed in claim 3, wherein the dispersing agent is an acrylic graft copolymer with nonionic surface active properties.

5. An emulsion as claimed in claim 1, wherein the stabiliser has a molecular weight of from about 400 to $10^4$.

6. An emulsion as claimed in claim 1 wherein the stabilizer is a polystyrene, a polyolefin, a polybutadiene, a polypropylene glycol, methyl oleate, a polyalkyl(meth) acrylate, a polyvinylester, a polystyrene/ethylhexylacrylate copolymer, or a polyvinyl chloride.

7. An emulsion as claimed in claim 1, wherein the stabiliser is miscible with the discontinuous phase in any proportion.

8. An emulsion as claimed in claim 1, wherein the discontinuous phase comprises a non-aqueous solvent.

9. An emulsion as claimed in claim 8, wherein the non aqueous solvent is xylene, a propyl benzene fraction, dihydroisophorone or an alkyl naphthalene fraction.

10. A method of preparing a stable concentrated emulsion composition comprising a continuous aqueous phase and a discontinuous non-aqueous phase which discontinuous phase comprises a substance capable of transport through the aqueous phase to cause Ostwald ripening of the emulsion, which method comprises emulsifying a non-aqueous phase comprising the said substance and a dissolved stabilizer that is soluble in the discontinuous phase, but less than 10 ppm soluble in and not transportable through the aqueous continuous phase and has a molecular weight of at least 250 to about 10,000, in water in the presence of a surfactant, wherein the stabilizer is present in an amount sufficient to diminish or prevent Ostwald ripening of the emulsion.

11. A method as claimed in claim 10, wherein the non-aqueous phase includes a pesticide.

12. A method of preparing a stable emulsion composition comprising a continuous aqueous phase and a discontinuous non-aqueous phase which discontinuous phase comprises a first substance capable of transport through the aqueous phase to cause Ostwald ripening of the emulsion, which method comprises the steps of a) emulsifying in water in the presence of a surfactant a non-aqueous mixture comprising a stabilizer, but not containing said first substance, wherein the stabilizer is a second substance that is soluble in the discontinuous phase, but less than 10 ppm soluble in and not transportable through the aqueous continuous chase and has a molecular weight of at least 250 to about $10^6$, and wherein the amount of stabilizer present is sufficient to diminish or prevent Ostwald ripening of the emulsion composition prepared to obtain a template emulsion; and b) combining said first substance with said template emulsion.

13. A method as claimed in claim 12 wherein the first substance comprises a pesticide.

14. A method as claimed in claim 12 wherein the non-aqueous phase of the composition prepared includes a non-aqueous solvent.

15. A method as claimed in claim 14, wherein the non-aqueous solvent is xylene, a propyl benzene fraction, or an alkyl naphthalene fraction.

16. A method as claimed in claim 12, wherein said first substance is added to said template emulsion (a) without dilution or (b) in the form of a solution of the said first substance in a non-aqueous solvent.

17. A method as claimed in claim 16, wherein the said combining is carried out in a metered in-line mixing plant.

18. A method of preparing microcapsules, which method comprises preparing a stable emulsion composition by the method of claim 12 and, thereafter, producing microcapsules from the emulsion composition thus prepared by a polycondensation or coacervation process.

19. A method according to claim 18 wherein the first substance comprises a pesticide.

* * * * *

UNITED STATES PATENT AND TRADEMARK OFFICE
CERTIFICATE OF CORRECTION

PATENT NO : 6,074,986

DATED : June 13, 2000

INVENTOR(S) : Patrick Joseph Mulqueen, Steven Duff Lubetkin, Graham Banks, Andrew Mark Fowles It is certified that error appears in the above-identified patent and that said Letters Patent are hereby corrected as shown below:

Claim 12, Line 15, "chase" should read - phase --.

Signed and Sealed this

Twenty-seventh Day of March, 2001

*Attest:*

NICHOLAS P. GODICI

*Attesting Officer*

*Acting Director of the United States Patent and Trademark Office*